US010526627B2

(12) United States Patent
Skuratowicz et al.

(10) Patent No.: US 10,526,627 B2
(45) Date of Patent: Jan. 7, 2020

(54) METHOD FOR PRODUCING HIGH MOLECULAR WEIGHT REDUCED VISCOSITY STARCH PASTES

(75) Inventors: Roman Skuratowicz, Hickory Hills, IL (US); Mathew Rice, Riverside, IL (US); Aaren Stubberfield, Chicago, IL (US); Philip Strong, Chicago, IL (US)

(73) Assignee: Corn Products Development, Inc, Westchester, IL (US)

( * ) Notice: Subject to any disclaimer, the term of this patent is extended or adjusted under 35 U.S.C. 154(b) by 0 days.

(21) Appl. No.: 12/323,710

(22) Filed: Nov. 26, 2008

(65) Prior Publication Data

US 2009/0142812 A1 Jun. 4, 2009

Related U.S. Application Data (60) Provisional application No. 60/991,349, filed on Nov. 30, 2007.

(51) Int. Cl.
*C12P 19/14* (2006.01)

(52) U.S. Cl.
CPC .................................. *C12P 19/14* (2013.01)

(58) Field of Classification Search
CPC ....................................................... C12P 19/14
See application file for complete search history.

(56) References Cited

U.S. PATENT DOCUMENTS

| 2,516,632 | A | * | 7/1950 | Kesler et al. | 536/111 |
| 3,458,395 | A | * | 7/1969 | Stalker | 162/175 |
| 3,620,842 | A | * | 11/1971 | Germino et al. | 127/32 |
| 3,783,100 | A | * | 1/1974 | Larson et al. | 435/95 |
| 4,052,226 | A | * | 10/1977 | Verbanac | 127/29 |
| 4,211,842 | A | * | 7/1980 | Marshall | 435/210 |
| 4,540,663 | A | * | 9/1985 | Witt | 435/99 |
| 4,575,487 | A | | 3/1986 | Shetty et al. | |
| 4,603,110 | A | | 7/1986 | Morehouse et al. | |
| 4,689,296 | A | * | 8/1987 | Chiang et al. | 435/97 |
| 4,957,563 | A | * | 9/1990 | Gallaher et al. | 127/38 |
| 5,131,953 | A | | 7/1992 | Kasica et al. | |
| 5,176,927 | A | | 1/1993 | Haarasilta et al. | |
| 5,180,669 | A | * | 1/1993 | Antrim | 435/99 |
| 5,318,635 | A | | 6/1994 | Kasica et al. | |
| 5,622,749 | A | * | 4/1997 | Rohringer et al. | 427/158 |
| 5,681,826 | A | * | 10/1997 | Shibuya et al. | 514/54 |
| 5,840,108 | A | | 11/1998 | Karras et al. | |
| 6,022,450 | A | * | 2/2000 | Van Kessel et al. | 162/174 |
| 6,129,788 | A | * | 10/2000 | Liaw et al. | 127/40 |
| 7,033,626 | B2 | | 4/2006 | Spender et al. | |
| 7,229,801 | B2 | | 6/2007 | Fujii et al. | |
| 2003/0029444 | A1 | | 2/2003 | Carbone et al. | |
| 2004/0115778 | A1 | | 6/2004 | Fujii et al. | |
| 2004/0166201 | A1 | | 8/2004 | Nielsen et al. | |
| 2005/0031734 | A1 | * | 2/2005 | Duan et al. | 426/20 |
| 2006/0188631 | A1 | | 8/2006 | Woo et al. | |
| 2006/0240099 | A1 | | 10/2006 | Carbone et al. | |

FOREIGN PATENT DOCUMENTS

| EP | 0252730 | * | 1/1988 |
| WO | WO 98/45417 | * | 10/1998 |
| WO | WO 00/12746 | * | 3/2000 |

OTHER PUBLICATIONS

Megazyme, alpha-glucosidase (transglucosidase) [online], 2011 [retrieved on Dec. 10, 2011]. Retrieved from the Internet:<URL:http://www.megazyme.com/Dynamic.aspx?control=CSViewProduct&categoryName=Enzymes&productId=E-TRNGL>, 1 page.*
Ao et al., J Agric. Food chem., 2007, Vo. 55, p. 4550-4547.*
Beier et al., Protein Engineering, 2000, vol. 13, No. 7, p. 509-513.*
Einde et al., JFS, 2003, vol. 68, No. 8, p. 2396-2404.*
Ratnayake et al., Journal of Agricultural and Food Chemistry, 2006, vol. 54, No. 10, p. 3712-3716.*
Takeuchi, T., "Histochemical Demonstration of Branching Enzyme (Amylo-1,4→1,6-Transglucosidase) in Animal Tissues," *J Histochem Cytochem*, 1958, 6:208, pp. 208-216.
Calzyme Laboratories, Inc., "alpha-Glucosidase," printed Oct. 17, 2011, 3 pages; http://www.calzyme.com/commerce/catalog/spcategory.jsp?category_id=1005.

* cited by examiner

*Primary Examiner* — Kade Ariani
(74) *Attorney, Agent, or Firm* — Jacquelin Cohen; Jason Grauch; Rachael Casey (57) ABSTRACT

Disclosed herein are methods of making high molecular weight, reduced viscosity starch pastes by enzymatic conversion. The methods provide a process for producing enzyme-thinned starch pastes that have improved molecular weight distributions, i.e., starch pastes having a more mid to high molecular weight content and less low molecular weight sugars than traditional enzyme converted pastes at similar solids and viscosity. In some embodiments, the methods utilize an enzyme capable of producing longer-chain oligosaccharides rather than low-molecular weight sugars. Other embodiments utilize a combination of enzymes to provide low viscosity pastes that are stabilized against setback and retrogradation. Furthermore, the methods may utilize a continuous starch enzyme cooker for the production of the high molecular weight, reduced viscosity starch pastes.

19 Claims, 6 Drawing Sheets

METHOD FOR PRODUCING HIGH MOLECULAR WEIGHT REDUCED VISCOSITY STARCH PASTES

CROSS-REFERENCE TO RELATED APPLICATIONS

This application claims priority to U.S. Provisional Patent Application No. 60/991,349, filed Nov. 30, 2007, the entire contents of which are hereby incorporated by reference in its entirety.

TECHNICAL FIELD

The present technology relates generally to the field of modified starches. In particular, the present technology relates to methods of preparing low viscosity modified starch pastes having a high molecular weight distribution using novel enzyme mixtures in an enzymatic starch conversion process.

BACKGROUND

The following description is provided to assist the understanding of the reader. None of the information provided or references cited is admitted to be prior art to the present invention.

Starch enzymes such as amylases are currently used to make starch hydrolysates. Starch hydrolysates are used in the production of maltodextrins, corn syrups and sugars, and to make low viscosity starch pastes. The primary application for these pastes is in papermaking for size press or coating. High solids starch pastes are typically prepared either by chemical thinning or enzymatic conversion, which lower paste viscosity allowing higher solids to be used. In the latter use, starch hydrolytic enzymes, such as amylases, are added at doses and conditions sufficient to reduce the molecular weight of the cooked starch, but to maintain the composition primarily as a starch paste rather than a hydrolysate of mostly sugars. As a result, these pastes have high molecular weight components, which provide strength and film properties to the starch paste, but they also have a lower viscosity than unmodified starch pastes, meaning that pastes of higher solids can be made flowable or pumpable under typical operating conditions.

Under some conditions, starch pastes, especially acid thinned starch pastes, exhibit retrogradation and setback. Setback refers to the viscosity increase of a paste as temperature is lowered. Retrogradation refers to the irreversible insolubilization of starch paste with formation of a precipitate or gel depending on the concentration. Retrogradation is mainly due to the presence of amylose in the starch. The linear amylose molecules are attracted to each other and form bundles of parallel polysaccharide chains by the formation of hydrogen bonds between hydroxyl groups on neighboring molecules. The tendency of amylose molecules to retrograde is increased by molecular weight reduction to a chain length of around 100 glucose units. Amylopectin having a branched structure shows less tendency to retrograde.

The setback and retrogradation properties of pastes are affected by the levels and lengths of amylose (linear) and amylopectin (branched) fractions in the starch pastes. Amylose in native corn starch comprises about 27% of the starch and has a molecular weight average of about 2 million atomic weight units (AWU). Amylopectin comprises about 73% of corn starch and has an estimated molecular weight of 10 million. Different sources of starch will have different sizes and distributions of amylose and amylopectin. Likewise, thinning reactions will change the sizes and proportion of these components. In addition, derivatization reactions can also add branches to these molecules, which can change their behavior, specifically relative to setback and retrogradation.

SUMMARY

The present disclosure relates to reduced viscosity starch pastes with improved molecular weight distributions prepared using enzymatic conversion. These pastes will have reduced levels of low molecular weight sugars, and increased levels of mid- to high-molecular weight components relative to currently used enzyme converted starches at similar paste solids and viscosities. In one aspect, the disclosure provides a method for producing a high molecular weight, reduced viscosity starch paste comprising: (a) heating a composition comprising starch and water at a temperature above the initial gelatinization temperature of the starch; (b) adding one or more starch hydrolyzing enzymes to the composition that preferentially produce long-chain oligosaccharides; (c) inactivating the enzyme in the paste; and (d) recovering the hydrolyzed starch paste, wherein the majority of the polymers in the paste have a molecular weight above about 10,000, a substantial proportion of the polymers have a molecular weight below about 200,000, and fewer polymers of have a molecular weight less than 10,000. The starch hydrolyzing enzymes are allowed to react with the starch for a period of time sufficient to hydrolyze and thin the starch in the composition. The typical outcome of this process is to make a starch paste with low levels of low molecular weight sugars and longer average chain lengths of molecules at specific solids and viscosity compared to conventional enzyme-converted starches. Paste properties can also be affected to provide higher or lower levels of setback and retrogradation. In a particular embodiment, a paste is produced in which at least about 20% of the polymers in the paste have a molecular weight from 10,000 to 200,000 and fewer than about 5%, fewer than about 4%, fewer than about 3%, fewer than about 2%, or fewer than about 1% of the polymers of have a molecular weight less than 10,000.

In one embodiment, the starch hydrolyzing enzyme has a random endoamylase activity. For example, the starch hydrolyzing enzyme may have greater endoamylase activity than exoamylase activity, thereby producing long-chain hydrolysis products rather than short, low molecular weight (i.e., less than about 10 DP) products. In one embodiment, the starch hydrolyzing enzyme is an α-amylase which hydrolyzes random α-D-1,4-glycosidic bonds in glucose polymers. In some embodiments, the starch hydrolyzing enzyme is an α-amylase from a *Bacillus* species, such as *Bacillus licheniformis*, which are more temperature stable than other enzymes. In a particular embodiment, the starch hydrolyzing enzyme is an endoamylase derived from *Bacillus licheniformis* sold under the tradename Speczyme® Xtra.

In one embodiment, the enzyme is added in an amount sufficient to produce a starch paste with a viscosity from about 50 to 200 cps at 80° C. at about 10% to about 25% solids. In a particular embodiment, the enzyme is added in an amount sufficient to produce a starch paste with a viscosity from about 50 to 200 cps at 80° C. at 16% solids. For example, the amount of enzyme added to the composition may be from about 15 to 25 ppm based on the starch, with an activity of approx 14,000 AAU/g (alpha amylase units/gram). Methods for assaying alpha-amylase activity are known in the art (See e.g., Genencor, Inc. website).

In some embodiments, the method further comprises providing an additional starch-modifying enzyme to the composition. Specific functionality can be applied to a cooked starch paste by reacting the paste with a particular enzymes or a combination of enzymes with specific functionality. These enzymes could be added simultaneously or as needed separately as parts of a multi-stage enzyme addition. In one embodiment, the starch modifying enzyme is α-amylase, beta amylase, glucoamylase, pullulanase, iso-amylase, transglucosidase, and mixtures thereof. In another embodiment, the starch modifying enzyme may be a starch synthesis enzyme, starch branching enzyme, or a transglucosidase enzyme. In particular, embodiments, the addition of a transglucosidase enzyme improves the viscosity stability of the starch paste as compared to starch pastes produced when no transglucosidase is added. In another embodiment, the methods further comprise the step of shearing the starch paste in order to further reduce the viscosity of the paste.

In one embodiment, the methods further comprise the step of inactivating the enzyme by reducing the pH, by increasing the temperature, by adding an inhibiting salt, or combinations thereof.

In various embodiments, the starch used in the methods is granular starch. In one embodiment, the starch is corn starch. In some embodiments, the starch is a chemically modified starch or a physically modified starch. A chemically modified starch may include, but is not limited to, a derivatized starch, a crosslinked starch, or a converted starch. In some embodiments, the starch is a physically modified starch. A physically modified starch may include, but is not limited to, a heat treated starch.

In some embodiments, the method is performed in a batch process. In other embodiments, the method is performed as a continuous process, e.g., in a continuous enzyme starch cooker.

In another aspect, the disclosure provides a method for producing a high molecular weight, reduced viscosity starch paste comprising: (a) heating a composition comprising starch and water at a temperature above the initial gelatinization temperature of the starch; (b) adding one or more starch hydrolyzing enzymes to the composition; (c) inactivating the one or more starch hydrolyzing enzymes; (d) adding a starch modifying enzyme, e.g., a transglucosidase or starch branching enzyme, to the composition; and (e) recovering the hydrolyzed starch paste, wherein at least about 20% of the polymers in the paste have a molecular weight from 10,000 to 200,000 and fewer than about 5% of the polymers of have a molecular weight less than 10,000. In some embodiments, the recovered starch paste has a lower setback and retrogradation, and reduced low molecular weight fractions compared to a starch paste where no transglucosidase is added.

In another aspect, the disclosure provides a continuous method for producing a high molecular weight, reduced viscosity starch paste comprising: (a) mixing a composition comprising granular starch and water; (b) adding one or more starch hydrolyzing enzymes to the composition, wherein the starch hydrolyzing enzymes preferentially produce long-chain oligosaccharides; (c) jet-cooking the composition of step (b) in a first jet-cooker to a temperature from about 160° F. to 210° F.; (d) maintaining the paste for a hold time of about 5 to 60 minutes, typically about 15 to 45 minutes, (e) following step (d), jet-cooking the composition in a second jet-cooker to a temperature from about 250° F. to 300° F. to denature the enzyme; and (f) recovering the hydrolyzed starch paste, wherein at least about 20% of the polymers in the paste have a molecular weight from 10,000 to 200,000 and fewer than about 5% of the polymers of have a molecular weight less than 10,000. In one embodiment, at least about 10%, at least about 15%, at least about 20%, at least about 25%, at least about 30%, at least about 40%, at least about 50% of the polymers have a molecular weight from 10,000 to 500,000 and fewer than about 10%, fewer than about 8%, fewer than about 5%, fewer than about 4%, fewer than about 3%, fewer than about 2%, or fewer than about 1% of the polymers have a molecular weight less than 10,000.

In one embodiment, the starting material for the process utilizes a starch slurry having a range of solids from about 5% to about 50%, from about 10% to about 45%, from about 20% to about 40%, or from about 25% to about 35%.

In one embodiment, calcium carbonate is added to the starch slurry as a pH buffer and improve enzyme activity. Calcium carbonate may be added at levels of 100-1200 ppm calcium relative to starch solids, typically about 300-600 ppm.

In another aspect, the present invention provides starch pastes having a high molecular weight reduced viscosity starch content produced using enzymatic thinning. In one embodiment, the starch paste is produced by: (a) mixing a composition comprising granular starch and water; (b) adding one or more starch hydrolyzing enzymes to the composition, wherein the starch hydrolyzing enzymes preferentially produce long-chain oligosaccharides; (c) jet-cooking the composition of step (b) in a first jet-cooker to a temperature from about 160° F. to 210° F.; (d) maintaining the paste in a plug flow reactor for a hold time of about 5 to 60 minutes, typically about 15 to 45 minutes, (e) following step (d), jet-cooking the composition in a second jet-cooker to a temperature from about 250° F. to 300° F. to denature the enzyme; and (f) recovering the hydrolyzed starch paste, wherein at least about 20% of the polymers in the paste have a molecular weight from 10,000 to 200,000 and fewer than about 5% of the polymers of have a molecular weight less than 10,000. In one embodiment, at least about 10%, at least about 15%, at least about 20%, at least about 25%, at least about 30%, at least about 40%, at least about 50% of the polymers have a molecular weight from 10,000 to 500,000 and fewer than about 10%, fewer than about 8%, fewer than about 5%, fewer than about 4%, fewer than about 3%, fewer than about 2%, or fewer than about 1% of the polymers have a molecular weight less than 10,000.

DETAILED DESCRIPTION

Disclosed herein are methods of making starch pastes with unique properties by enzymatic conversion. In particular, enzymatic methods of making starch pastes having a high molecular weight, low viscosity content are described.

The present inventors have discovered a process for producing enzyme-thinned starch pastes which have different properties than traditional enzyme converted pastes used by the paper industry. In particular, enzyme-converted pastes are described which have similar properties to acid-thinned starches, i.e., starch pastes having a large proportion of high molecular weight material and which exhibit the characteristics of retrogradation and setback. Another example is a paste with improved viscosity stability, which has less retrogradation or viscosity growth in storage, but comprises predominantly higher molecular weight fractions of starch. In some embodiments, the methods of this invention involve heating an aqueous starch slurry to an elevated temperature with an enzyme capable of depolymerizing starch and holding the mixture at the elevated temperature for a time to gelatinize the starch granules and produce a starch paste of desired viscosity. The reaction can occur in a continuous or a batch process.

For many applications, enzyme thinning technology aims to reduce setback and retrogradation of starch pastes. Attempts to reduce these characteristics comes at the cost of creating large fractions of low molecular weight "sugar" components. This is because many hydrolytic enzymes function to create sugars from starch, and the thinning of the starch paste viscosity is a secondary effect. Therefore, the present invention provides methods, which yield starch pastes having different and unexpected properties than those of typical enzyme-converted starch pastes. For some applications, such as gypsum manufacture, mining applications, and food applications, starches having high setback and retrogradation are desirable. These applications prefer a paste that will form rigid gels upon cooling.

Other applications require stable viscosity and higher molecular weight fractions. Consequently, low molecular weight "sugar" fractions will act as a diluent or contaminant. For these applications, pastes must not only exhibit higher molecular weight distributions at a given solids and viscosity, but must also have relatively low linear amylose fractions, and consequently do not exhibit properties of setback and retrogradation.

To create starch pastes having an increased proportion of high molecular weight material, the methods utilize enzymes which selectively hydrolyze starch polymers to produce starch pastes with significant amounts of mid-molecular weight materials ranging from about 25,000 to about 200,000 MW units. These pastes further exhibit the characteristics of higher setback and retrogradation. While not wishing to be limited to any particular mechanism, the enzymes used in the methods randomly hydrolyze starch polymers, resulting in faster viscosity reduction compared to enzymes typically used in enzymatic conversion methods. In one embodiment, the enzymes are sterically hindered from systematic cleavage of sugar chains from starch molecules, and as a result, are forced to make more random cleavage of larger chains. In another embodiment, enzymes specifically attack certain linkages such as specific 1-4 linkages starch chains. They also produce fewer low molecular weight sugar fractions than traditional enzyme-thinned pastes at similar solids levels. By reducing the low molecular weight sugar fraction, and increasing medium molecular weight amylose fractions, these pastes have performance properties similar to many commercially produced modified starches, primarily acid thinned starches.

Because of the higher amount of amylose-like materials, these pastes have dramatically higher setback and retrogradation than similar viscosity pastes made with traditional amylases. As a result, these would not be useful in applications such as adhesives and papermaking without further additives or chemical treatment. However, these pastes are useful in applications including, but not limited to, gypsum manufacture, mining applications, and certain food applications. When applied in a continuous enzyme starch cooker, the methods allow for the use of less costly unmodified starch as a replacement for more expensive modified starch.

In one embodiment, enzyme-thinned pastes are produced that exhibit the characteristics of dextrin pastes. Dextrins are starches which are usually produced by dry roasting the starch in the presence of acid catalysts to form low viscosity highly branched materials. These pastes have very low viscosity relative to starch pastes at similar solids, but because of the highly branched nature of the dextrins, they exhibit more viscosity stability and a lower tendency to retrograde or setback. The dry roasting process leads to higher branching, and fewer low molecular weight fractions under 10,000. To create enzyme-converted starch pastes that behave like dextrin pastes, combinations of certain types of cleavage and conversion enzymes are used, such as α-amylase and transglucosidase. One example is a combination of amylase and a transglucosidase to reduce viscosity and to transfer glucose units or chains to branches on the starch. This would allow the formation of starch pastes which resemble dextrin pastes.

The following definitions are herein provided to facilitate understanding of the invention. The terms defined below are more fully defined by reference to the specification as a whole. Units, prefixes, and symbols may be denoted in their accepted SI form.

The term "acid-thinned starch" as used herein refers to a starch preparation treated with dilute acid at a temperature below the gelatinization point. Typically, this results in a reduction in the average molecular size of the starch polymers. Acid-thinned starches tend to have a much lower hot viscosity than native starch and a strong tendency to gel when cooled.

The term "degree of polymerization" or "DP" of a polymer as used herein refers to the average number of monomer units in the molecule. When applied to starch, amylose, or amylopectin, DP refers to the number of glucose units in the molecule.

The term "enzyme-converted starch" or "enzyme-thinned starch" as used herein refers to the enzyme-catalyzed thinning of starch pastes used to reduce viscosity to a specific range.

The term "gelatinization" as used herein refers to the irreversible swelling of starch granules under the influence of heat and/or chemicals in an aqueous medium to give a starch paste. Viscosity rises and is at a peak when the granules are hydrated to their maximum extent. The "gelatinatization temperature" is the temperature at which a particular starch gelatinizes to form a starch paste. This depends on starch type, the gelatinization conditions, and several other factors. Normally, chemical stabilization alters the gelatinization temperature as does the solids content of the slurry.

The term "hydrolysis" as used herein refers to the chemical reaction of a molecule with water to produce two or more smaller molecules. Specific hydrolysis processes may be catalyzed by acids, alkalis, or enzymes according to type of reaction. Hydrolysis is the underlying reaction in the enzyme- or acid-catalyzed conversion of starch into maltodextrins, glucose syrups, and starch pastes. The degree of hydrolysis determines the final molecular weight and properties of the product. In one embodiment, hydrolysis of starch is catalyzed by an enzyme, e.g., an amylase enzyme.

The term "retrogradation" as used herein refers to the irreversible insolubilization of starch paste with formation of a precipitate or gel depending on concentration. Retrogradation is mainly due to the presence of amylose in the starch. The linear amylose molecules are attracted to each other and form bundles of parallel polysaccharide chains by the formation of hydrogen bonds between hydroxyl groups on neighboring molecules. The tendency of amylose molecules to retrograde is increased by molecular weight reduction to a chain length of around 100 glucose units. Amylopectin having a branched structure shows less tendency to retrograde.

The term "setback" refers to the thickening of starch paste viscosity as temperature drops. This is mostly a reversible reaction, although retrogradation may also occur during cooling which affects the results measured as setback viscosity growth.

The term "starch paste" as used herein refers to the viscous colloidal mass resulting from the gelatinization of starch in water. A starch paste is not a solution but contains swollen granules, dissolved amylose, and a number of intermediate species. The stability of starch pastes depends on starch type, concentration and storage temperature, among other factors.

Starch Paste Properties

Starch is a carbohydrate polymer occurring in granular form certain plant species, including cereals and tubers, e.g., corn, wheat, rice, tapioca, potato, and pea. Starch exists in certain plant species in the form of small bundles known as granules. These granules have a characteristic size and shape depending on the particular source involved. Starch granule size is generally expressed as a range depending on the particular starch type e.g., corn starch granules are in the range 5-25 microns.

Starch consists of two polymers of linked D-glucose units-amylose and amylopectin. Amylopectin is the constituent of starch having a polymeric, branched structure. In addition to α-D-1,4 bonds, the amylopectin molecule has α-D-1,6 bonds which occur every 20-30 glucose units. Aqueous solutions of amylopectin are characterized by high viscosity, clarity, stability, and resistance to gelling. The level of amylopectin varies between different starch types. Amylose is the constituent of starch in which glucose units are linked by α-D-1,4 glycosidic bonds to form linear chains. The amount of amylose and its molecular weight vary between different starch types. Amylose molecules are typically 200-2000 glucose units in length. Aqueous solutions of amylose are very unstable due to intermolecular attraction and association of neighboring amylose molecules. This leads to an increase in viscosity, retrogradation and, under specific conditions, precipitation of amylose particles.

The molecular weight of the constituent polymers, particularly amylose, varies between different starch sources. A single plant species may comprise various proportions of amylose and amylopectin, e.g., high amylose corn. All starches form viscous pastes when sufficiently cooked in water but there are significant differences in paste texture, viscosity, and stability.

Starch Sources

The granular starch to be processed in the methods may be obtained from tubers, roots, stems, legumes, cereals or whole grain. More specifically the source of granular starch includes, but is not limited to, corn kernels, wheat, barley, rye, milo, sago, cassava, tapioca, sorghum, rice, peas, bean, banana or potatoes. The granular starch to be processed may be a highly refined starch quality, e.g., more than 90%, 95%, 97% or 99% pure, or it may be a more crude starch containing material comprising milled whole grain including non-starch fractions such as germ residues and fibers.

The raw material, such as whole grain, is milled in order to open up the structure and allowing for further processing. Two milling processes include wet and dry milling. Dry milling uses the whole kernel. Wet milling separates the germ and meal (starch granules and protein). Both dry and wet milling are well known in the art of starch processing and are equally contemplated for the processes described herein. Starches may also be chemically or physically modified during manufacture or to change properties. Modified starches may also be used in this process. Examples of starch modifications include, but are not limited, to acid thinning, oxidation, hydroxyalkylation, esterification, cationization, dextrinization, carboxymethylation, grafting, extrusion, or crosslinking.

Production of Starch Pastes

Enzyme-converted starch pastes are typically prepared with a temperature stable enzyme being added to a starch slurry. The slurry is pasted and then allowed to react for a certain time. This is followed by a "kill" step, where high temperature of chemicals are used to denature the enzyme and stop the thinning reaction. Enzyme activity is often limited by a range of pH and temperature at which the enzyme functions.

In one embodiment, starch pastes are produced from granular starch in a batch process where a slurry/enzyme mix is heated and allowed to react. In one embodiment, steam is injected into the agitated slurry/enzyme mixture to paste the starch. The paste is allowed to react for its allotted time and the reaction is terminated by adjusting the pH to denature the enzyme.

In another embodiment, starch pastes are produced from granular starch using a continuous process. One system for the continuous enzymatic production of starch pastes is a continuous enzyme starch cooker (CESC). In this process, a makedown unit combines dry starch with water to make a consistent slurry ranging from about 1%-45% solids. In some embodiments, the starch slurry contains calcium carbonate at levels of about 100 to 1200 ppm, typically about 300 to 800 ppm. A dilute enzyme is metered into the slurry and thoroughly mixed with the slurry flow. The slurry and enzyme mixture is then sent through an inductor jet (cook jet) and mixed with steam to heat the slurry and enzyme to about 150° F.-220° F. This cooks the starch and heats the enzyme to its optimally-active temperature range. The flow of starch paste goes from the jet into the side of a plug flow enzyme reactor column which maintains a fixed reaction time. The starch exiting the plug flow reactor is then pumped through a kill jet (very similar to the cook jet), and heated with pressure and stem to about 250° F.-350° F. This heating process inactivates the enzyme. The paste is then sent to a flash chamber to bring it back down to atmospheric pressure and 212° F. The resulting paste can be further diluted or concentrated to the appropriate amount of solids, or stored for later use.

Enzymes

The primary enzyme used in thinning of starch pastes is α-amylase. This is available from a variety of biological sources, (bacteria, saliva, pancreatic, etc.) and in a variety of activity and stability levels. α-Amylases are enzymes which fragment starch chains by cleaving of 1,4-α-glycosidic bonds. These enzymes are also used to produce maltodextrins, syrups and dextrose. α-Amylase enzymes can have slightly different active sites, or may be sterically restricted in where on the starch molecules they can attach. Based on these differences as well as reaction conditions, different enzymes will have preference to make different molecular weight distributions in starch pastes at similar viscosities. Changing the ratio of enzyme to starch and time, temperature, shear, and pH of the reaction can affect the way enzymes break down starch.

There are many varieties of this α-amylase, but only a few varieties are used commercially based on their temperature and pH stability, reactivity, and the properties of the paste that they impart. For both paper and adhesive applications, one of the most important attributes is viscosity stability. In these applications, pastes are preferred, which have minimal setback, or viscosity growth as temperature decreases, and minimal retrogradation, or viscosity growth in storage at low temperatures. These attributes can be illustrated with a Brabender viscograph, which demonstrates the viscosity of pastes at different temperatures (see Example 1).

Enzymes currently used in paper and adhesives are designed to minimize setback and retrogradation in pastes. However, amylase enzymes ideally are designed to convert starch to low molecular weight sugars, and as a result, the more a paste is reacted with enzyme (either higher enzyme doses, longer reaction times, or a combination of both), the more low molecular weight sugars are formed. These sugars are readily measured by analyzing the molecular weight distribution of starch pastes. As starches are treated to higher levels of enzymes, they will have larger amounts of material in the lower molecular weight fractions. For example, the amount of polymers having molecular weights less than about 10,000 MW, less than about 5,000 MW, and less than about 1,000 MW is typically greater in conventional enzyme-thinned starches as a compared to acid-thinned starches.

Thus, in accordance with the present invention, enzymes and enzyme mixtures are provided which produce enzyme-thinned starches that exhibit properties of retrogradation and setback that are typically characteristic of acid-thinned starches. In certain embodiments, specific enzymes are used in combination or in place of traditional α-amylase enzymes to impart properties to the pastes that are unique. In one embodiment, an endoamylase enzyme is used which hydrolyzes internal α-1,4-glucosidic bonds. An endoamylase is an amylase that catalyzes the cleavage of α-1,4-glucosidic bonds not necessarily at the nonreducing end of the polysaccharide. By contrast, an exoamylase is an amylase that catalyzes the cleavage of α-1,4-glucosidic bonds only at the nonreducing termini of polysaccharide chains. Consequently, the hydrolysis products produced by an exoamylase are typically shorter oligosaccharides than those produced by an endoamylase. In a particular embodiment, the enzyme is an endoamylase which randomly cleaves α-1,4-glucosidic bonds in glucose polymers. An example of this type of enzyme is Spezyme® Xtra (Danisco).

In one embodiment, physical shear is used to facilitate additional random thinning and to reduce ordered enzymatic thinning. In another embodiment, random thinning is facilitated by using enzymes that have a propensity to reattach at adjacent molecules rather than systematically cleaving repeated saccharide units from a specific molecule. Optimizing these conditions along with the functional characteristics of the particular enzyme can be used to encourage a molecular weight distribution and paste properties that are similar to more expensive modified starches.

In another embodiment, specific functional enzymes are used in combination or in place of α-amylase enzymes to impart properties to the pastes that are unique. In one embodiment, a mixture of α-amylases with pullulanase, or debranching enzyme would both reduce viscosity and break amylopectin branches into short chain fragments. In suitable embodiments, these combinations alter paste behavior and molecular weight distribution to paste similar to modified starches with high setback, such as acid thinned starch.

In one embodiment, the amount of enzyme used will produce a starch paste having the desired viscosity, but will not produce a large amount of low molecular weight sugars, i.e., oligosaccharides having a DP less than about 10, less than about 5, or less than about 2.

The optimal dosage level of the enzyme depends upon processing parameters such as raw material, viscosity, processing time, pH, temperature, and the percent solids. In one embodiment, the enzyme is added in an amount sufficient to produce a starch paste with a viscosity from about 50 to 1000 cps, from about 50 to 500 cps, from about 50 to 250 cps, or from about 50 to 200 cps at (measured at 80° C. and 16% solids).

In one embodiment, thinned starch pastes with improved viscosity and temperature stability can be made in a process utilizing a combination of two types of enzymes. An α-amylase may be used as the primary method of viscosity reduction, and a branching enzyme may be added to act as a both a scavenger for low molecular weight by-products and to branch the low molecular weight components and starch chains to each other in various combinations.

In one embodiment, a temperature-stabilized enzyme is first blended with starch slurry with any pH buffers suitable to maintain the slurry within the active range of the enzyme. The slurry is heated to about 170-220° F. in order to gelatinize the starch and allow the enzyme to begin breaking down the high molecular weight material. A second branching enzyme, such as transglucosidase, can be added at various points in the process depending on that enzymes' temperature stability. Enzymes with higher temperature stability can be added with the α-amylase. Enzymes requiring lower temperature stability could be added after the α-amylase reduced paste viscosity to a point where the paste temperature can be lowered with a heat exchanger or other suitable means. The amount of thinning required by the α-amylase prior to temperature reduction and branching enzyme addition is dependent on the solids content of the slurry, and the viscosity limitations of the reaction equipment. If a continuous reactor is used, then the starch paste will need to be thinned to a suitable viscosity for proper dispersion of the enzyme and proper flow of the paste with pumping equipment.

The second reaction is allowed to proceed until the starch paste reaches its preferred final viscosity, during which time the branching enzyme would have sufficient time to branch starch chains to each other and to low molecular weight sugars created by amylase thinning. The paste is then treated to suitably denature the enzymes, e.g., by heat, acid, or another method. The resulting paste will have reduced viscosity compared to untreated starch paste at similar solids and temperature, but will also have superior viscosity stability because of the branched components introduced by the branching enzyme.

In one embodiment, the amount of enzyme used in relation to the starch is higher than amounts normally used in known enzyme starch conversion processes while shorter conversion times are used. For example, about 10 to 1000 ppm enzyme relative to starch may be added, preferably about 15 to 600 ppm, and more preferably about 15 to 150 ppm. Reaction times may also be lower compared to typical times of about 20 to 40 minutes. Accordingly, in suitable embodiments, a reaction time will be about 2 to 20 minutes. With the use of high enzyme dosages and short conversion times, the adverse effects of contamination on the effectiveness of the starch depolymerizing enzyme is minimized. Once the enzyme has been allowed to act on the starch for a sufficient length of time, the starch-enzyme mixture is further heated and held at an elevated temperature for a time sufficient to inactivate the enzyme. Finally, a starch paste having a desired and substantially stable viscosity is recovered.

EXAMPLES

The present invention is further illustrated by the following examples, which should not be construed as limiting in any way.

Example 1

Pasting Analysis of Acid Thinned and Oxidized Starches

In this Example, the properties of starch pastes produced by acid thinning or oxidation were analyzed. For each sample, 500 g of starch slurry was prepared at 14% solids and adjusted to pH 7-8. The slurry was placed in a Brabender Viscograph E and treated with the following temperature profile: Heat at 1.5° C./min from 50° C. to 95° C., hold for 30 minutes, cool at 1.5° C./min to 50° C. and hold for 30 min. Viscosities are in Brabender units, and the mixing speed was 75 rpm. Brabender Viscometers and methods are available from C. W. Brabender Instruments, Inc. (South Hackensack, N.J.).

Figure 1:
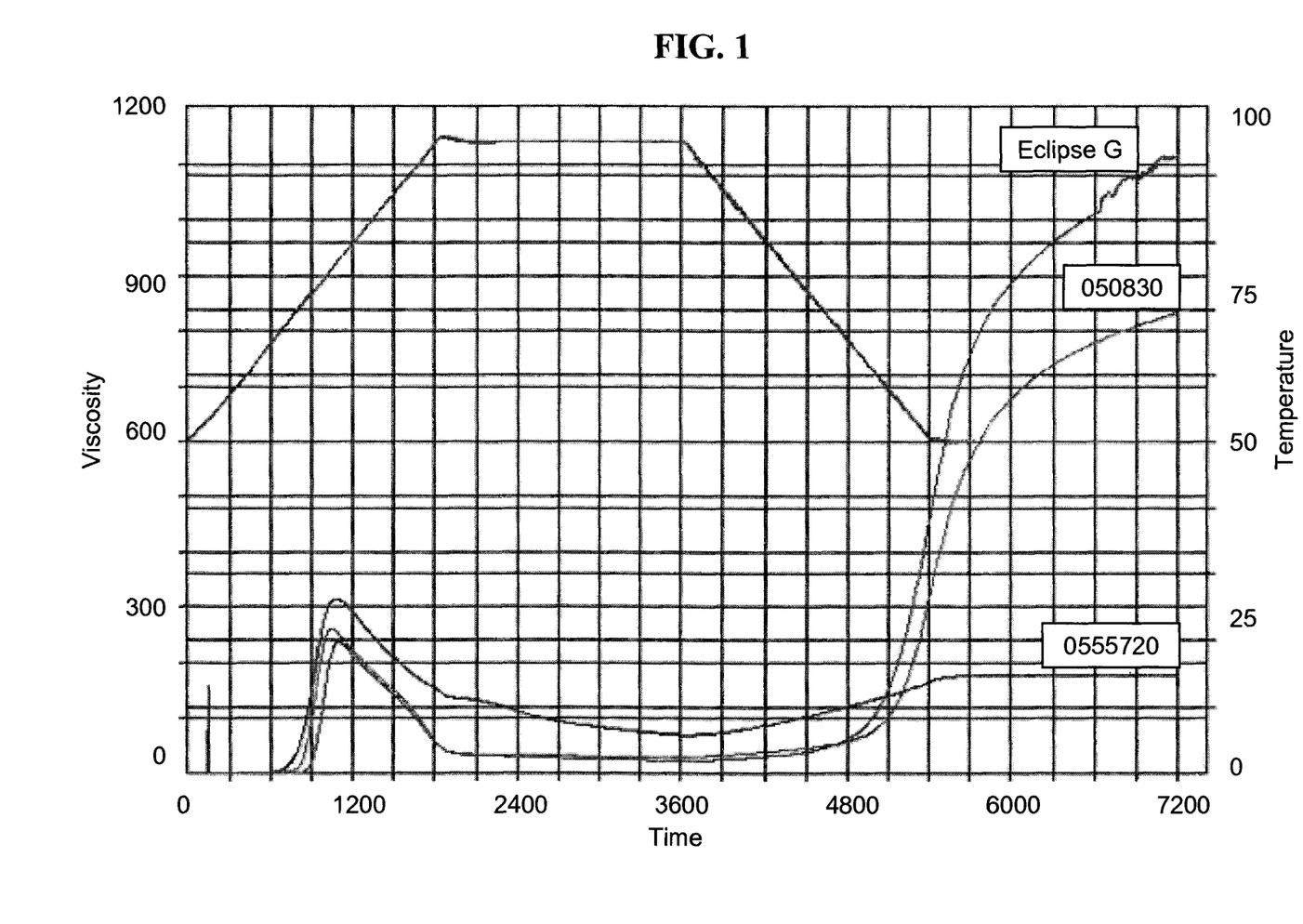
FIG. 1 is a graph showing the Brabender analysis of an oxidized starch and two acid-thinned starch pastes. The graph shows the viscosities of the starches over a range of temperatures.

The samples included two acid thinned starches (Corn Products 050830 and Tate and Lyle Eclipse G) and an oxidized starch (Corn Products 055720) all of which were converted to similar levels during manufacture. The results are shown in FIG. 1 and summarized in Table 1. The temperature at which viscosity builds during the initial heating is the gelatinization temperature. The maximum viscosity achieved during the cooking is the peak viscosity, and the temperature at which the maximum viscosity is reached is the peak temperature. Viscosities were also measured at the 95° C. and 50° C. initial and 30 min points.

TABLE 1

Brabender Analysis of Acid-Thinned and Oxidized Starches

| | | | | | Viscosity (Brabaender units) | | | |
|---|---|---|---|---|---|---|---|---|
| Sample | Starch Type | Gel Temp | Peak V | Peak T | 95° C. | 95° C. 30 min | 50° C. | 50° C. 30 min |
| 050830 | Acid thinned | 70.5 | 261 | 76 | 58 | 30 | 317 | 833 |
| 055720 | Oxidized | 53.3 | 315 | 76.7 | 153 | 71 | 165 | 178 |
| Eclipse G | Acid thinned | 72.2 | 237 | 77.2 | 57 | 25 | 458 | 1111 |

Paste stability is affected by setback and retrogradation. Setback is the change in viscosity relative to change in temperature during cooling. Thus, setback is shown by the difference in viscosity between the 95° C. 30 min point and the 50° C. point. The acid-thinned starch samples both exhibited significantly higher setback than the oxidized starch sample.

Retrogradation is the thickening of starch pastes on storage at cooler temperatures. Thus, retrogradation is shown by the difference between the 50° C. and 50° C. 30 min. The acid thinned starch samples both exhibited significantly higher retrogradation than the oxidized starch sample. In these examples, enzyme converted starch is not used because the product is converted in situ. The enzyme converted starch commercially used in paper and adhesive applications shows significantly less setback and retrogradation than acid thinned starch, but measurably more than an oxidized starch.

Example 2

Molecular Weight Distributions of Enzyme Converted Starch Pastes

In this Example, the molecular weight distributions of various samples of enzyme-thinned pastes were analyzed. A paste of the starch or dextrin was made at about 5% solids (or diluted if a paste was made by in situ enzyme conversion) and this was diluted 1 to 10 with dimethylsulfoxide (DMSO). The samples were fractionated on a size exclusion chromatography (SEC) system and analyzed for molecular weight distribution. The SEC system consisted of two Synchropak GPC500 and one GPC100 silica columns available from Eprogen (Darien, Ill.). Eluent was a 75:25 mixture of DMSO and 0.002 M aqueous potassium phosphate at pH 7. The elution rate was 0.2 ml/min and the system temperature was 50° C. with refractive index detection. Results are presented as distributions based on molecular weight as compared to linear pullulan standards by retention time. Molecular weight values assume linear molecules, so the values are representative of molecular size rather than true molecular weight.

Figure 2:
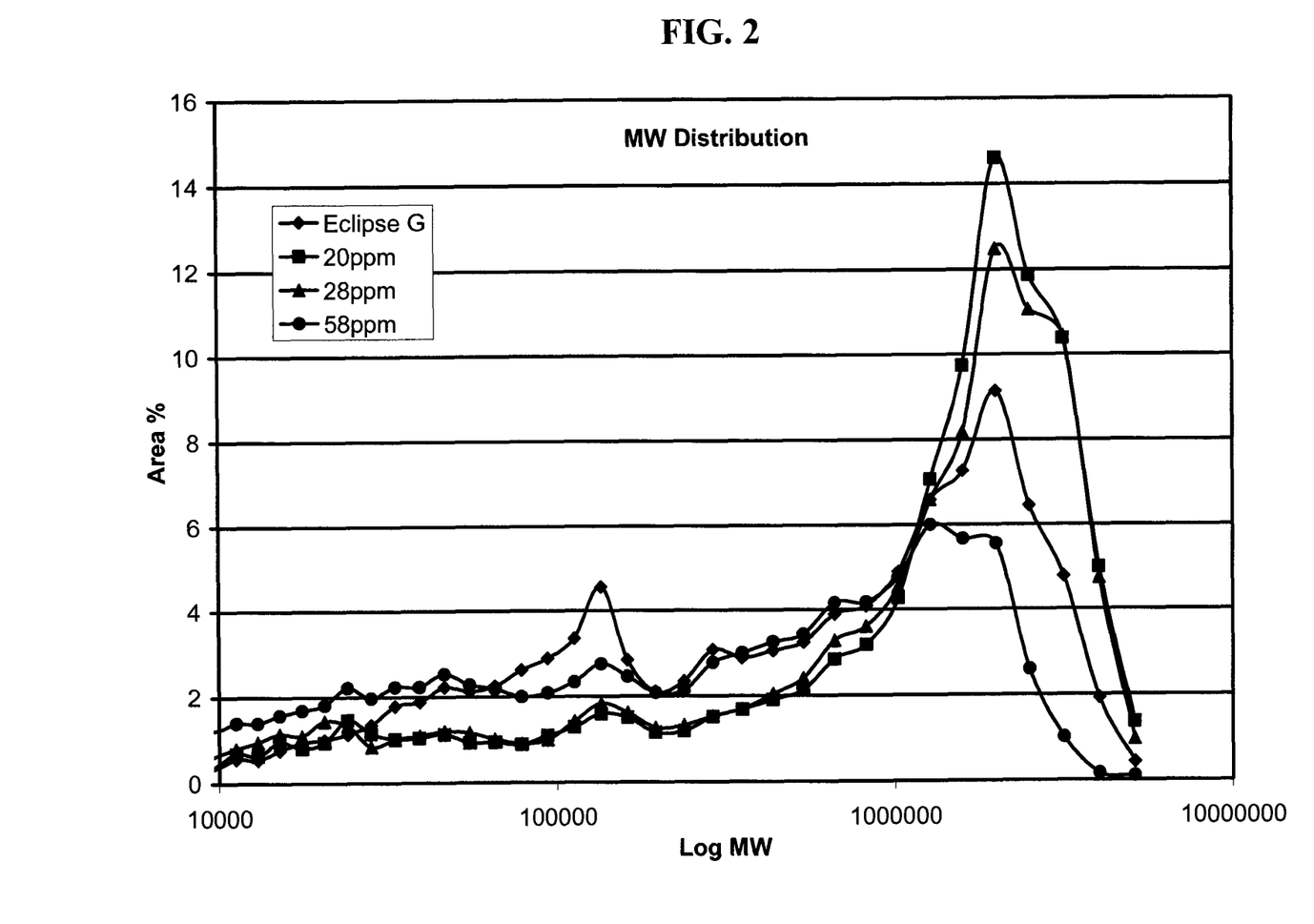
FIG. 2 is a graph of the results of size exclusion chromatography showing the molecular weight distribution of an acid-thinned starch paste (Eclipse G) and three enzyme-converted starch pastes treated with different amounts of enzyme.

In one experiment, different amounts of enzyme were added to produce a starch paste. Samples included Eclipse G (a pasted acid-thinned starch with no enzyme conversion) and pastes produced using 20, 28, and 58 ppm of α-amylase enzyme with unmodified corn starch. The enzyme in these experiments was VisCoat™ (Danisco), an amylase used commercially by the paper industry. The results are shown in FIG. 2. The data indicate that acid-thinned starch has significantly more material in the mid-molecular weight range (at the peak near 100,000 MW) compared to the enzyme-thinned starches. Likewise, the enzyme-thinned starches show more low molecular weight material than the acid-thinned starch-particularly, in the 58 ppm sample. These data indicate that traditional enzymes used for enzyme thinning produce very different starch pastes as compared to acid-thinned starches.

Figure 3:
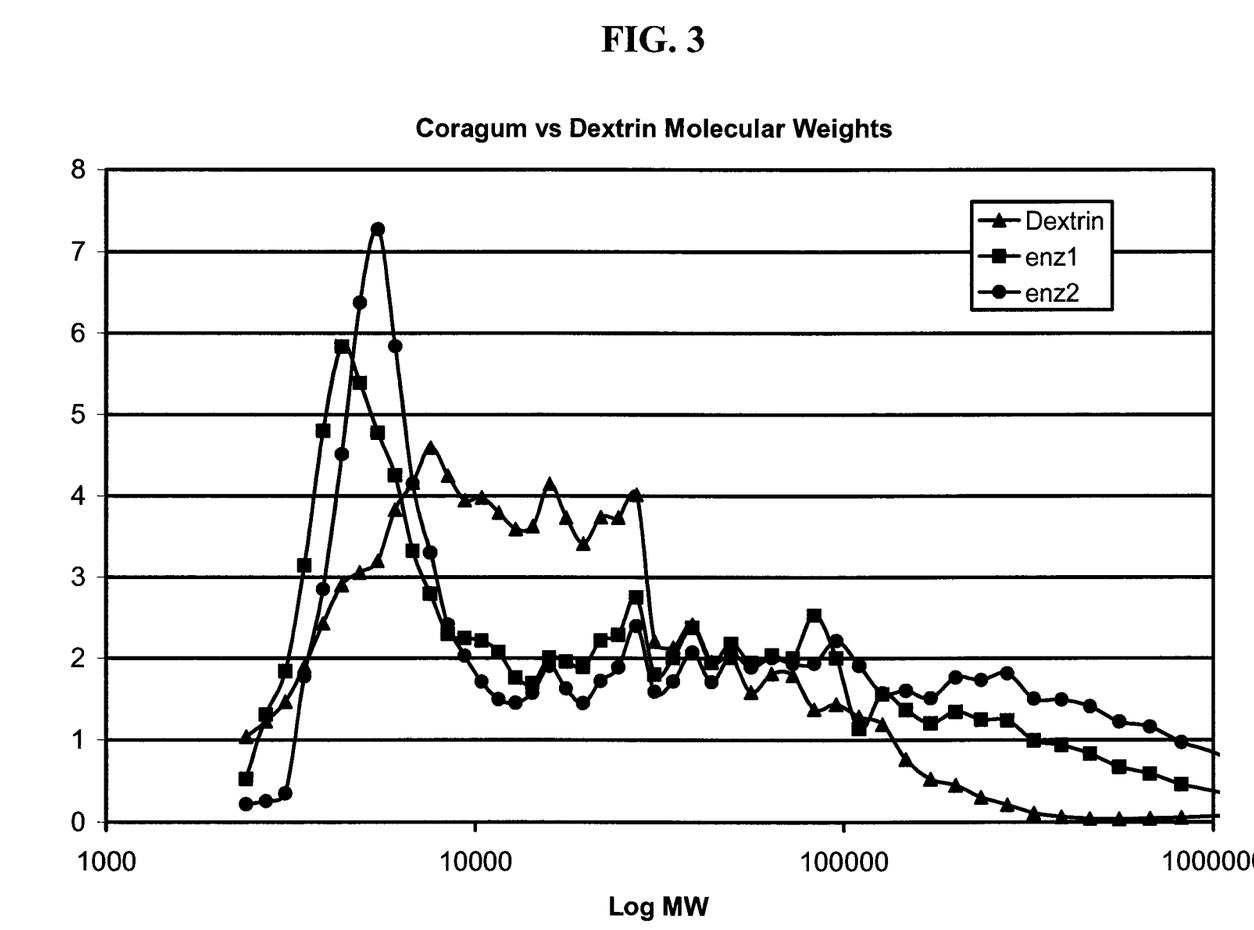
FIG. 3 is a graph of the results of size exclusion chromatography showing the molecular weight distribution of a dextrin paste and two enzyme-converted starch pastes.

In another experiment, two pastes were produced with very high enzyme dosages and the molecular weight of these pastes was compared to a dextrin paste (Corn Products 070610). These enzyme converted pastes were likewise made with VisCoat™ enzyme but at levels of 200-300 ppm based on starch. The results are shown in FIG. 3 and indicate that a large low molecular weight peak is formed by enzyme thinning at these dosages. These enzyme-converted pastes would not have the performance of the high molecular weight dextrin pastes (which have similar viscosity at a given solids) since the low molecular weight material would act as a diluent.

Example 3

Enzyme Converted Starches Having Properties of Acid-Thinned Starches

The molecular weight distributions of three starch pastes were compared: an acid-thinned starch paste; an enzyme-converted starch paste prepared using VisCoat™ (Danisco); and an enzyme-converted starch paste prepared using Spezyme® Xtra (Danisco). VisCoat™ enzyme is a commercially used liquid α-amylase from a genetically modified strain of *Bacillus amyloliquefaciens*. VisCoat™ enzyme hydrolyzes internal 1,4-α-D-glucosyl linkages of gelatinized starch. Spezyme® Xtra enzyme is an α-amylase that is derived from a genetically modified strain of *Bacillus licheniformis*. The endoamylase in Spezyme® Xtra randomly hydrolyzes α-1,4-glucosidic bonds to quickly reduce the viscosity of gelatinized starch, producing soluble dextrins and oligosaccharides under a variety of process conditions.

The acid-thinned starch of 70 fluidity (Casco 050820) was jet cooked at 280° F. and was used as a reference sample. The remaining two pastes were made by enzyme converting unmodified starch (Corn Products 030050) in a boiling water bath. These samples were prepared by pasting 55 grams starch with 0.8 grams calcium carbonate in 290 grams total solution. The enzyme was diluted and added at doses to get approximately 100 cps at 80° C. Viscoat™ enzyme was added at a dosage of 1 g of a 1% solution and Spezyme® at 0.25 g of a 0.5% solution. Both were stirred for 5 minutes and allowed to sit covered for an additional 10 minutes in the boiling water bath. The samples were treated with dilute hydrochloric acid to reduce pH below 4 to stop enzyme activity. Viscosity was analyzed with a Brookfield SSB viscometer, 20 rpm and 80° C. The Viscoat™ sample produced a paste with a viscosity of 85 cps and the Spezyme® paste produced a paste with a viscosity of 120 cps.

To analyze the molecular weight distribution, pastes were diluted to 7% solids and 10 grams of the dilutions were dissolved in 90 mL of DMSO. The samples were fractionated on a size exclusion chromatograph as described above.

Figure 4:
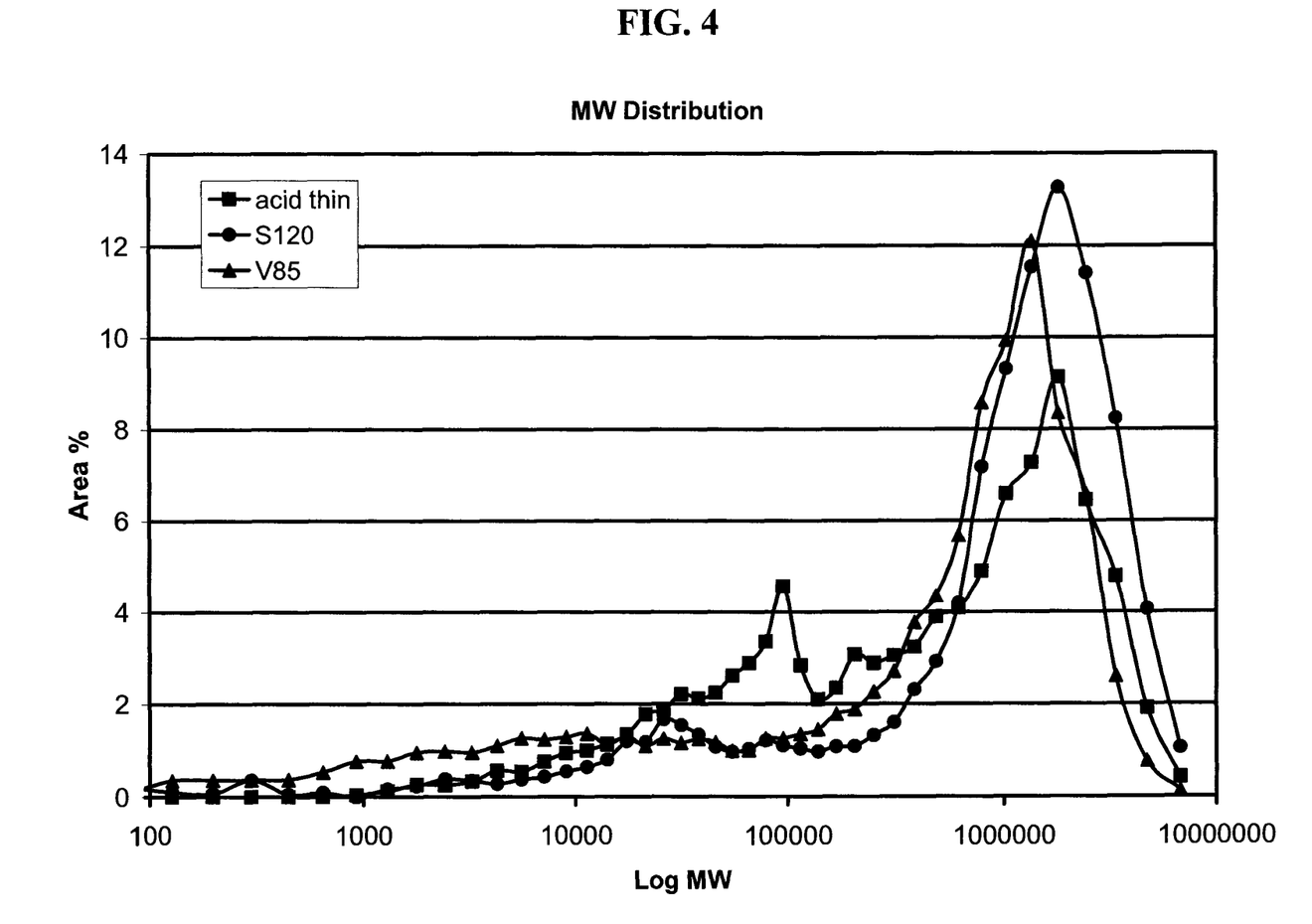
FIG. 4 is a graph of the results of size exclusion chromatography showing the molecular weight distribution of an acid-thinned starch paste and two enzyme-converted starch pastes using two different types of α-amylase enzymes.

The results are shown in FIG. 4. The chromatogram shows that the acid-thinned starch has a mid-range peak in the 10,000-200,000 MW range. The VisCoat™ paste (V85) shows most of the reduced molecular weight material is distributed over a wide range between 100-100,000 MW. Compared to VisCoat™ paste, the Spezyme® paste (S120) has a significant amount of material in the 10,000-100,000 MW range, and very little material in the sub-5,000 MW range. This is despite the fact that both pastes having similar viscosity. In addition, the Spezyme® paste demonstrated considerably more setback on storage than the VisCoat™ paste, becoming a solid gel by the time it reached room temperature. The VisCoat™ paste remained fluid as it cooled to room temperature. This demonstrates how specific enzyme choice can alter the molecular weight distribution of starch pastes and thereby provide different paste attributes.

Figure 5:
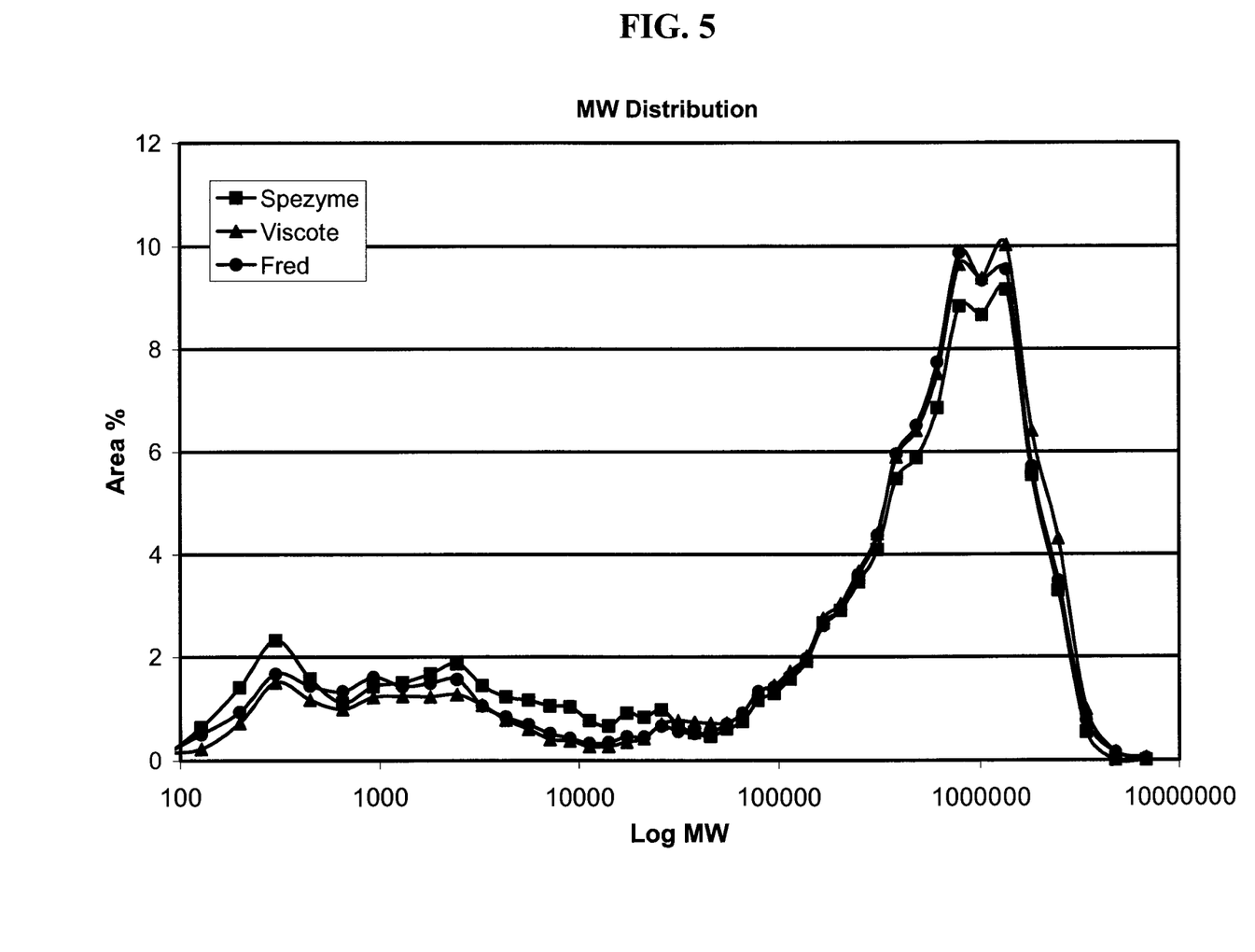
FIG. 5 is a graph of the results of size exclusion chromatography showing the molecular weight distribution of enzyme-converted starch pastes using three different types of α-amylase enzymes.

The molecular weight distribution the VisCoat™ paste was compared to the Spezyme® Xtra paste and a Spezyme® FRED (Danisco) paste, produced as described above. As shown in FIG. 5, both the Spezyme® Xtra (Spezyme) paste and the Spezyme® FRED (Fred) paste exhibited significantly more material in the 10,000-100,000 MW range compared to the VisCoat™ paste.

Example 5

Molecular Weight Distributions of Transglucosylase-Treated Starch Pastes

A starch slurry at 20% solids and buffered to pH 7, with 600 ppm calcium carbonate as an enzyme stabilizer, was reacted with 12 ppm α-amylase (Viscote from Danisco) by jet cooking the slurry to 190° F., and holding in a plug flow reactor for 20 minutes. Next, the α-amylase was denatured by jet cooking at 280° F. The resulting paste had solids of approximately 15.5%. A 7% solids dilution of this paste exhibits a viscosity of approximately 35 cps at 150° F. The paste was cooled to 140° F. and reacted with a dilute transglucosidase (Genencor) at a dosage of 5 grams of enzyme to 800 grams paste. The enzyme was allowed to react at 140° F. for up to 24 hours. Samples were collected at various times, dissolved in DMSO to make 90:10 ratio of DMSO to water, 1% total solids, and then analyzed by size exclusion chromatography. Chromatography was performed with refractive index detection, and separation on Eichrom GPC columns using a DMSO water eluent and characterized against pullulan molecular weight standards.

Figure 6:
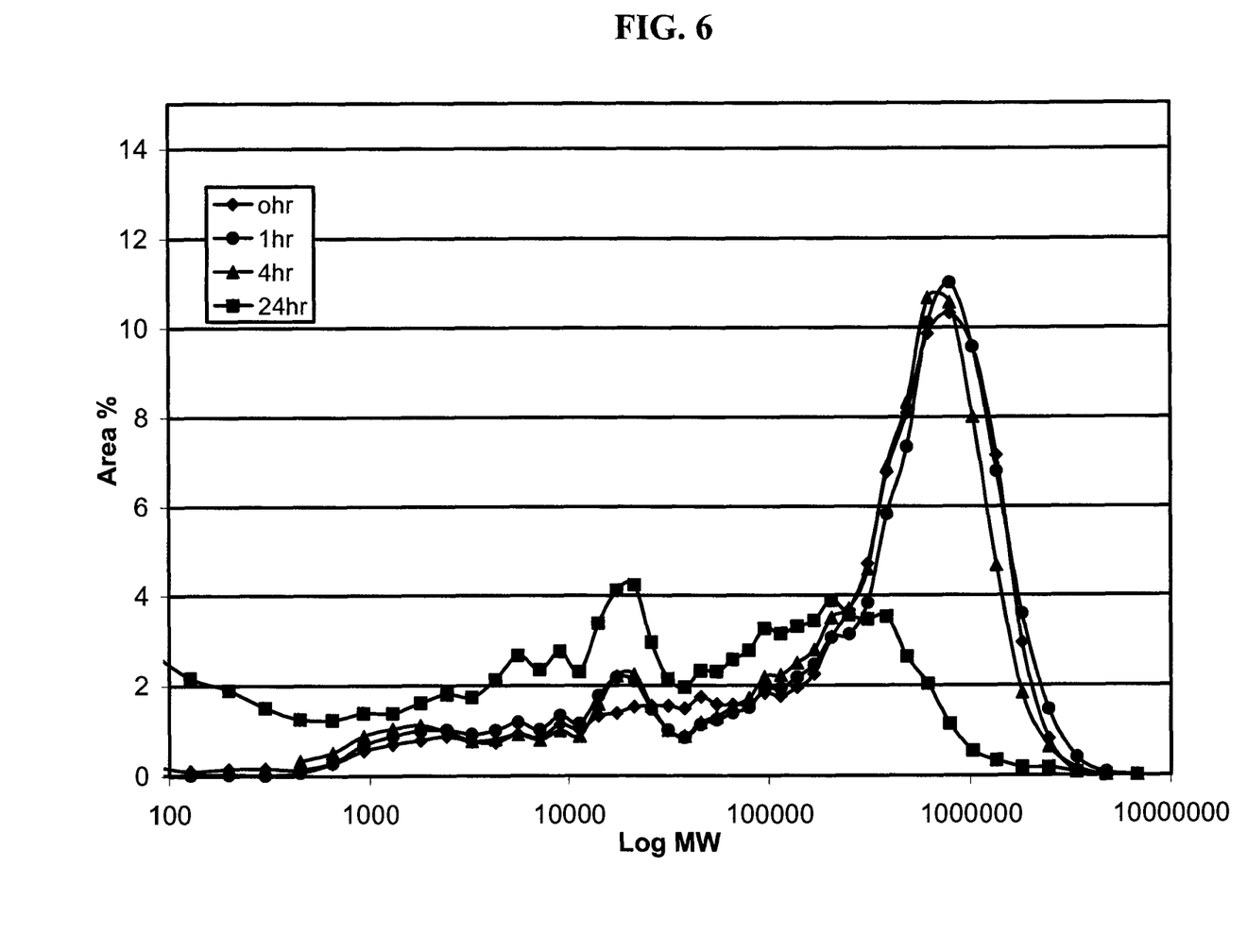
FIG. 6 is a graph of the results of size exclusion chromatography showing the molecular weight distribution of an α-amylase thinned starch (15% solids) to which a five gram dose of transglucosidase was added. Analyses were taken after 0, 1, 4, and 24 hours.

The data are shown in FIG. 6. As the reaction proceeds with the dilute transglucosidase, the lower molecular weight fractions begin to decrease while a medium molecular weight fraction form and begin to increase in weight percent (1,000-10,000 MW range). As the reaction continues to 24 hours, there is a substantial drop in high molecular weight material because the crude transglucosidase that was used has substantial amounts of α-amylase which begin to compete with the branching activity of transglucosidase. These effects could be mitigated using a purified fraction of transglucosidase.

EQUIVALENTS

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

All publications, patent applications, patents, and other references mentioned herein are expressly incorporated by reference in their entirety, to the same extent as if each were incorporated by reference individually.

Other embodiments are set forth within the following claims.

What is claimed is:

1. A method for producing a high molecular weight, hydrolyzed, reduced viscosity starch paste comprising:
   (a) heating a composition comprising starch and water at a temperature sufficient to gelatinize the starch;
   (b) adding one or more starch hydrolyzing enzymes wherein at least one of the starch hydrolyzing enzymes has endoamylase activity,
   (c) adding a transaglucosidase enzyme,
      wherein the enzymes added to the composition produce long-chain oligosaccharides;
   (d) inactivating the enzymes in the paste; and
   (e) recovering the hydrolyzed, reduced viscosity starch paste, wherein at least 20% by weight of the starch hydrolysates in the paste have a molecular weight distribution from 10,000 to 200,000 and fewer than 5% by weight of the starch hydrolysates have a molecular weight distribution less than 10,000.

2. The method of claim 1, wherein at least one starch hydrolyzing enzyme added in step (b) is an α-amylase which hydrolyzes random a-D-1,4-glycosidic bonds in glucose polymers.

3. The method of claim 2, wherein the α-amylase added in step (b) is an endoamylase derived from *Bacillus licheniformis*.

4. The method of claim 3, wherein the one or more starch hydrolyzing enzymes of step (b) is added in an amount sufficient to produce a starch paste with a viscosity from about 50 to 500 cps at 80° C. at about 10% to 25% solids.

5. The method of claim 4, wherein the one or more starch hydrolyzing enzymes of step (b) is added in an amount sufficient to produce a starch paste with a viscosity from about 50 to 500 cps at 80° C. at about 16% solids.

6. The method of claim 1, further comprising a step of adding a starch modifying enzyme.

7. The method of claim 6, wherein the starch modifying enzyme is selected from the group consisting of: α-amylase, beta amylase, glucoamylase, pullulanase, isoamylase, and mixtures thereof.

8. The composition of claim 7, wherein the starch modifying enzyme is added after inactivating the one or more starch hydrolyzing enzymes having endoamylase activity.

9. The method of claim 1, wherein the recovered starch paste has a lower setback and retrogradation compared to a starch paste where no transglucosidase is added.

10. The method of claim 1, further comprising the step of shearing the starch paste in order to further reduce the viscosity of the paste.

11. The method of claim 1, wherein the enzymes are inactivated by reducing the pH, by increasing the temperature, by adding an inhibiting salt, or combinations thereof.

12. The method of claim 1, wherein the starch of step (a) is a chemically modified starch or a physically modified starch.

13. The method of claim 12, wherein the chemically modified starch is a derivatized starch, a crosslinked starch, or a converted starch.

14. The method of claim 12, wherein the physically modified starch is a heat treated starch.

15. A method for producing a high molecular weight, hydrolyzed, reduced viscosity starch paste comprising:
   (a) heating a composition comprising starch and water at a temperature sufficient to gelatinize the starch;
   (b) adding one or more starch hydrolyzing enzymes to the composition, wherein at least one of the starch hydrolyzing enzymes has endoamylase activity;
   (c) inactivating the one or more starch hydrolyzing enzymes;
   (d) adding a transglucosidase enzyme to the composition; and
   (e) recovering the hydrolyzed, reduced viscosity starch paste, wherein at least 20% by weight of the starch hydrolysates in the paste have a molecular weight distribution from 10,000 to 200,000 and fewer than 5% by weight of the starch hydrolysates have a molecular weight distribution less than 10,000.

16. The method of claim 15, wherein the recovered starch paste has a lower setback and retrogradation compared to a starch paste where no transglucosidase is added.

17. A continuous method for producing a high molecular weight, hydrolyzed, reduced viscosity starch paste comprising:
   (a) mixing a composition comprising granular starch and water to prepare a composition comprised of starch solids;
   (b) adding starch hydrolyzing enzymes to the composition, wherein the starch hydrolyzing enzymes have endoamylase and transglucosidase activities, and produce long-chain oligosaccharides;
   (c) jet-cooking the composition of step (b) in a first jet-cooker to a temperature from about 160° F. to 210° F.;
   (d) maintaining the composition for a hold time from about 5 to 60 minutes;
   (e) jet-cooking the composition in a second jet-cooker to a temperature of from about 250° F. to 300° F.;
   (f) recovering the hydrolyzed, reduced viscosity starch paste, wherein at least 20% by weight of the starch hydrolysates in the paste have a molecular weight distribution from 10,000 to 200,000 and fewer than 5% by weight of the starch hydrolysates have a molecular weight distribution less than 10,000.

18. The method of claim 17, wherein the composition further comprises calcium carbonate.

19. The method of claim 18, wherein the calcium carbonate is added from about 100 to 1200 ppm calcium relative to starch solids.

* * * * *